United States Patent [19]
Eils et al.

[11] Patent Number: 4,974,248
[45] Date of Patent: Nov. 27, 1990

[54] X-RAY SYSTEM FOR X-RAY DIAGNOSIS AND/OR X-RAY TREATMENT

[75] Inventors: Friedrich Eils, Wagnefeld; Wolfgang Müller, Espelkamp; Eli J. Schneider, Espelkamp; Peter Taubitz, Espelkamp; Ernst Knipping, Lübbecke, all of Fed. Rep. of Germany

[73] Assignee: Picker International GmbH, München, Fed. Rep. of Germany

[21] Appl. No.: 183,752
[22] PCT Filed: Jul. 23, 1987
[86] PCT No.: PCT/DE87/00332
§ 371 Date: May 2, 1988
§ 102(e) Date: May 2, 1988
[87] PCT Pub. No.: WO88/00789
PCT Pub. Date: Jan. 28, 1988

[30] Foreign Application Priority Data

Jul. 23, 1986 [DE] Fed. Rep. of Germany ....... 3624901

[51] Int. Cl.$^5$ .............................. H05G 1/64
[52] U.S. Cl. ......................... 378/98; 378/99
[58] Field of Search .................... 378/98, 99

[56] References Cited

U.S. PATENT DOCUMENTS

| | | | |
|---|---|---|---|
| 3,916,192 | 10/1975 | Schmitmann et al. | 378/98 |
| 3,932,759 | 1/1976 | Brundin | 378/98 |
| 3,999,044 | 12/1976 | Grim | 378/98 |
| 4,044,264 | 8/1977 | Lutz et al. | 378/98 |
| 4,097,793 | 6/1978 | Shapiro et al. | 378/98 |
| 4,158,138 | 6/1979 | Hellstrom | 378/98 |
| 4,160,906 | 7/1979 | Daniels et al. | 378/98 |
| 4,247,777 | 1/1981 | Pfeifer et al. | 378/98 |
| 4,255,662 | 3/1981 | Waterkamp | 378/98 |
| 4,553,254 | 11/1985 | Bach et al. | 378/98 |

FOREIGN PATENT DOCUMENTS

| | | |
|---|---|---|
| 2151890 | 7/1985 | European Pat. Off. . |
| 0201891 | 11/1986 | European Pat. Off. .............. 378/98 |
| 2220444 | 11/1973 | Fed. Rep. of Germany . |
| 0001640 | 5/1979 | Fed. Rep. of Germany . |
| 3324537 | 2/1984 | Fed. Rep. of Germany . |
| 3330116 | 5/1984 | Fed. Rep. of Germany . |

Primary Examiner—Janice A. Howell
Assistant Examiner—David P. Porta
Attorney, Agent, or Firm—Timothy B. Gurin

[57] ABSTRACT

X-Ray system for X-ray diagnosis and/or X-Ray treatment with a control console having control keys that serve in particular to retrieve from a program register organ-related programmed reference values for an X-Ray generator and an attached X-Ray machine, with a display device on the control console. The display device is embodied as a multiplace alphanumeric display device, into which the contents of the storage zones of a text storage area can be called as plain language text through actuation of switches and control keys. In particular, organ-related texts, errors, status messages and infrequently recalled operational data, can be retrieved. The display device can furthermore be connected to a test and diagnostic system or to a switch junction matrix, so that test programs for electronic modules, components or new output connections can be selected through interactive communication using the display device.

7 Claims, 1 Drawing Sheet

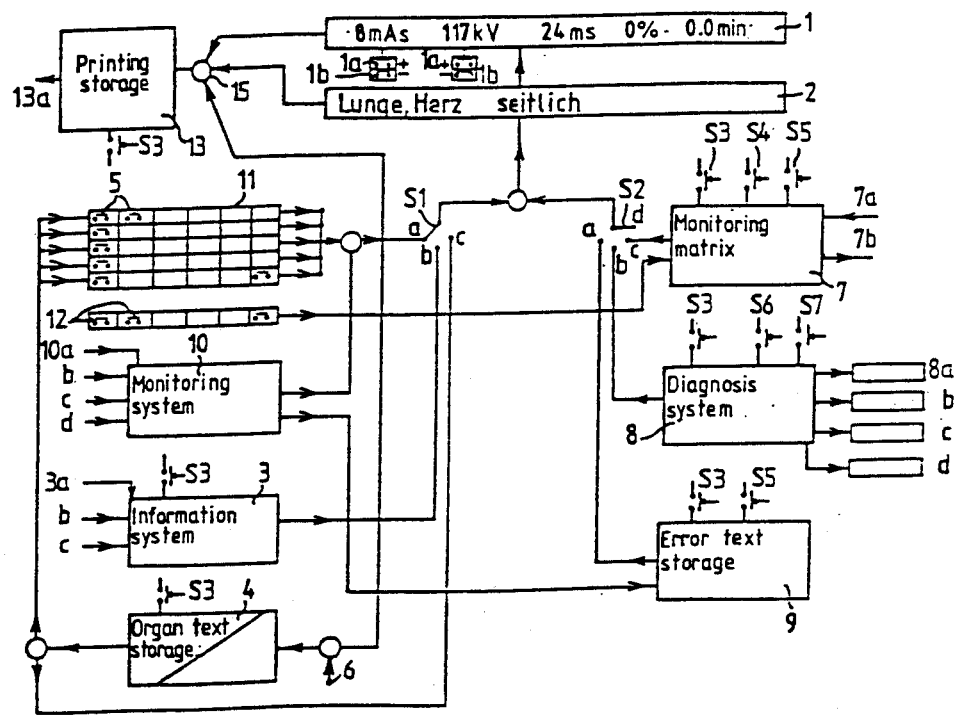

X-RAY SYSTEM FOR X-RAY DIAGNOSIS AND/OR X-RAY TREATMENT

The invention relates to an X-Ray system for X-Ray diagnosis and/or treatment. The invention relates preferably to a system for X-Ray diagnosis.

In a known X-Ray diagnosis system (DE-AS 23 11 211) function keys are arranged on a control console for retrieving from a program register preprogrammed reference inputs for an X-Ray generator and a connected X-Ray diagnostic apparatus. The reference values retrieved by a given function key are stored in the storage zone of the program storage to which this button is assigned and when the latter is pressed, such reference inputs are indicated on a display device located on the control console. The display device comprises numeric display fields used to indicate voltage at the X-Ray tube and the mas product, as well as indicator lamps to show any additional entered functions. It is also possible to freely choose the reference inputs for the X-Ray generator and the X-Ray diagnostic system through input members assigned to the display members of the display device as well as to store the chosen input values in appropriate storage zones of the program register by actuating a programming switch and one of the function keys.

It is therefore necessary to label the function keys according to given anatomic organ relations by marking the corresponding "organ text" on the description strip for the function key in question, such texts, owing to a lack of space on such description strips, being renderable only in short form. This could lead to the wrong function key being pressed, the result of which being the entry of an inappropriate or incorrect value for the type of diagnosis being performed. Such inputs, merely on account of their lengths, are often represented in cryptic form at the display device and on the indicator lamps, at the expense of accurate labelling of the body part being diagnosed.

In known X-Ray systems of the preceding type, indicator lamps can also show whether operator or system error has occurred, or whether the X-Ray generator or the attached radiograph apparatus is ready to operate according to the entered radiograph parameter values. In this connection, the reason for system unpreparedness or the error condition, can be determined from error lists, operating instructions or similar material that assist the operator in taking corrective action.

Hence, the invention provides for the development of an X-Ray system for X-Ray diagnosis and/or X-Ray treatment designed to provide clear and intelligible information for ease of operation and preferably also for maintenance and repair.

According to the invention a text storage area forms part of an X-Ray system for X-Ray diagnosis and/or X-Ray treatment while at a control console of the X-Ray system is located a multiplace alphanumeric single or multidigit display device, to which information memorized in a text storage unit can be recalled either automatically or by the actuation of switches, particularly control keys of the control console, at which display device such information is displayed uncoded and in plain language text incorporating longer and if required, more words.

The program register, in particular, comprises stored-related reference values that can be called from the program register by function keys located on the control console, and a text storage area for storing an organ-related word text assigned to a given function key. When the function key is pressed, the -related word text and the related reference values are indicated in the alphanumeric display device according to size, type and/or dimension. By means of a start switch, the corresponding reference data can be input and the related radiography or treatment session initiated. The invention permits reference values retrieved by the function keys to be more fully represented in the alphanumeric display device by using designated organ-related texts (e.g. "Skull observation a.p./p.a.", "Skull, lateral", "Skull a.p.", "Knee joint", "Frick's knee joint", than would be possible on the text strips of the control keys.

The invention includes an embodiment form of an X-Ray system of the type first mentioned in which the reference values are not retrieved from storage by means of function keys, but rather are input separately. Hence, pressing the appropriate function key results in the retrieval of only the organ-related texts from the storage. It is preferable, however, that in the program register, not only the organ-related texts, but also at least-related standard reference values be stored and retrievable by means of the function keys. In this connection it is preferable to have input devices through which standard reference values for radiographs retrieved from the program register can be freely modified, without such modifications affecting the stored standard reference values.

In a known manner, the program register can be programmed with-related reference values and their related organ-related texts. In addition to the program register, there should exist an auxiliary storage unit for organ-related texts and their related reference values. Thus, the system can switch from the program register to the auxiliary storage area through a switch arrangement, from which auxiliary storage area combinations of-related reference values and their corresponding organ-related texts under program control can be routed in serial fashion to the alphanumeric display device by means of a recall key and when the appropriate function key is-pressed, such a combination can be routed into the storage area of the program register relating to that key. Thus, the operator can, if need be, match by himself function keys to reference values and organ-related texts.

This embodiment furthermore permits the addition of a keyboard for programming the auxiliary storage area. Independently of the availability of the auxiliary storage area, there exists the possibility of attaching a keyboard for the alphanumeric display device. In both cases, the keyboard permits the operator, through the auxiliary storage or the display device, to route to the program register an organ-related text that would seem to the operator to be the quickest and clearest description of the body part assignment for a given function key. Should either the part of the display device indicating the organ-related texts or the part of an auxiliary storage area storing the organ-related texts be independently controllable through the keyboard by either the part of the auxiliary storage indicating or the part storing the reference values, the keyboard will permit freely formulated organ-related texts to be memorized and assigned to the stored and displayed reference values without causing the latter to be modified.

Alternatively or preferably, in an X-Ray system of the previously mentioned type with an electronic monitoring system capable of monitoring system readiness, operator or hardware error, exceeding or not attaining acceptable limit values, the monitoring system can be connected to a text storage area to which can be connected the multiplace alphanumeric display device program controlled by the monitoring system. This embodiment would permit the display device to display information relating to the type or causes of, different system malfunctions, such as, e.g. "saturation" if X-Ray tube voltage is allowed to become too high, or "operator error", whereby these occurences are presented in plain language text. The system can also present error correction prompts in plain language text, e.g. "close door", "turn on overload release", "turn generator on/off", which can be implemented in the interactive mode under program control. Consultation of error condition lists or the operating manual thus becomes superfluous. The monitoring texts can be so displayed that other indicated data are overridden by them. In addition, should a particular case so require, the monitoring device will not allow the system to perform a radiograph session until an error condition is corrected.

It is also preferred that the text storage unit of the monitoring system be connected to an error-text dump, in which an error or a similar item autonomously identifies itself upon its occurence, and which can be connected through a switch arrangement and a retrieval key to the display device. Maintenance or repair personnel are thus able to read in plain text the status of the error condition in question.

In a further embodiment of the invention, the display device can be connected through a key arrangement to a text storage area of an electronic information system, from which, by means of a retrieval key, certain data such as infrequently displayed operational parameters, (which if required can be program controlled by interaction), e.g. photo-timer data, data on film being used, counts of radiographs made, operation time, date, time, etc can be routed to the display device to appear in plain text.

In another embodiment of the invention, the display device and a keyboard may, if required, be connected to a print buffer when an appropriate switch is pressed, whose contents, by means of a retrieval switch, can be printed out on a printer, especially a label printer, thus permitting that, at the end of an X-Ray session, all radiograph data and previously submitted personal data are displayed by the printer, a procedure formerly performed by hand.

Alternatively or preferably, in addition to a program register and/or the text storage of a monitoring system of the type mentioned above, the multiplace alphanumeric display device can through a key arrangement and a selection switch be connected to a checklist printer assigned to an electronic test system integrated in the X-Ray system. Thus, the status of program-controlled electric modules and components, signal emitters and the like can be retrieved and through the assigned checklist storer and with the aid of the plain-text display device, local and function tests of e.g. storage, signal input and output, component groups and overall system functioning can be performed in the interactive mode. Interactive capability coupled with the display of error correction prompts in plain text simplify the technician's task of analysis and error correction. External test and service apparatus are thus not required.

Alternatively or preferably in addition to the already described embodiments of the invention, several X-Ray apparatuses within an X-Ray system for X-Ray diagnosis and/or X-Ray treatment, connectable by a common console through an appropriate switch to the X-Ray generator and the necessary function groups, are connected by means of a switch junction matrix. Switchovers in this switch junction matrix can be program controlled and initiated through a switch arrangement. To the switch junction, furthermore, is assigned a switch junction text storage area, the contents of whose storage zones are accessed under program control and routed to the display device through the switch arrangement when the control switches are actuated and figure in the interactive mode when a certain key combination is used, so that the appropriate plain language texts can appear in the display device.

In known X-Ray systems, different devices can be adapted to each other only through the use of bridges or by soldering data wires, etc. The programmable switch junction matrix according to the invention, on the other hand, can, with the aid of the alphanumeric display device, ensure the modification of switching connections in the interactive communication mode by displaying user-friendly textual information.

A currently preferred embodiment of the invention is illustrated by the attached drawing. In this regard, essentially only those X-Ray system components are shown, by which the alphanumeric display device on the operating console can be controlled.

The display device forming an integral part of the service portion of the X-Ray generator in embodiment example two features single-digit display fields 1 and 2, in which, in concert with the text storage area, longer instructions and information can, when certain switches are actuated be displayed in plain text under program control.

In the embodiment example shown, display field 1 can indicate all of the inputtable X-Ray generator reference values for a given radiograph, such as X-Ray tube voltage, mas product, illumination period, etc. In the drawing are shown for example knobs 1a and 1b, by means of which such reference values can be manually modified. Display field 2, on the other hand, is designed to display textual information, which if required for interactive communication can be retrieved from storage areas according to the position of selection switches S1 and S2 connected thereto.

Thus, when switch S1 is in the position indicated by S1-a, the alphanumeric display device indicates in plain language text any reference values executed or to be executed, texts, limit values, existing operator and system error conditions etc., whereby the operator and the maintenance technician are spared the task of consulting the instruction manual.

In addition to the above-mentioned plain text display, further texts can be called to the display device 1, 2 in order to aid the system operator. When integrated information system 3 is selected, operating parameters not normally displayed, such as radiograph counts from the radiograph counter, data on film being used, operating time, date, time, etc., can be indicated in plain language text in the display device 1, 2. The selection of an auxiliary storage unit for organ-related texts 4 permits by means of a program register 11 the matching of any organ-related text to any function key 5., or, the storage of new organ-related texts by the use of a keyboard interface 6.

The maintenance technician, moreover, can by reversing switch S2 carry out system parameter matches and signal assignments for peripheral apparatuses, in particular those selectable from the service console, as well as interrogate an integrated electronic diagnosis system 8 for testing electronic modules, signals or component groups and preprogrammed test programs. He can also request error status messages by regulating the error text auxiliary storage unit. In this case as well, operating instructions and other data are indicated in plain text.

In the original position S1-a of switch S1, a program register 11 for storing organ-programmed reference values and the appropriate organ-related texts which are retrievable by the actuation of a corresponding function key 5, and the text storage of an integrated electronic monitoring system 10, are selected separately.

Under the guidance of the electronic monitoring system are recorded through its inputs 10a to 10d, e.g. operator errors, system errors, limit values and generator functions, which are indicated in plain language text in display field 2 of the display device by the automatic recall of the appropriate monitoring texts from a monitoring text storage area.

When switch S1 is in position S1-b, electronic information system 3 is selected. When retrieval key S3 is pressed, all of the infrequently displayed operational parameters that are interactively program controlled, for example photo timer data, film types, radiograph count, operating time, date, time etc., can be retrieved through inputs 3a to 3c, and are presented in plain language text in display field 2.

When switch S1 is in position S1-c, the auxiliary storage area 4 for organ-related texts is selected. Related selector button S3 permits the assignment of any organ-related text (plain language text) in organ-related text storage areas to any function key, or the memorization of new organ-related texts by means of the keyboard interface. An additional interface 15 permits all radiograph data and personal data previously entered through the keyboard 6 to be downloaded into a printer storage device 13 from which, after the end of a radiograph session, such information can be output on a label printer or a similar device through output 13a.

In addition to operational data, maintenance technicians and installation personnel can interactively input other data in plain language text by pressing key S2. When switch S-2 is set in position S2-a, error text dump 9 is selected, from which, when read key S3 is pressed, error messages automatically recorded through the monitoring system 10 and its monitor text storage at the time of a given error condition are routed to display fields 1, 2 where they are presented in plain language. text. Thus, the technician keep abreast of current error conditions by reading plain language text.

The stored error messages can if required be deleted by pressing delete key S5.

When switch S2 is set to position S2-b, the test and diagnostic system forming an integral part of the X-Ray system, is selected. When selection key S3 is pressed, appropriate local or function tests on e.g. storage, signal in and outputs, component groups or functions 8a to 8d of the whole system, can be selected under program control. The procedure can be monitored through plain language interaction and displayed at the display device 1, 2. Pushbuttons S6 and S7, permit a given text to be either stopped or started under program control. Status information, or, if necessary error correction prompts, are displayed by the display device 1, 2 in plain language text.

When switch S2 is set to position S2-c, the junction matrix is selected in order to establish or break connections between inputs 7a and outputs 7b, and in particular with X-Ray apparatus selection keys 12. With the appropriate selection key S3 and through interaction with the display device 1, 2, preselection of switching connections can be performed and either confirmed or abandoned by use of pushbuttons S4 and S5. Items to be input in this case are limit values, tube adjustment and assignment of input and output signals for the connection of peripheral devices to the X-Ray generator. There is no need to replug or re-solder signal wires for peripheral devices, since the programmable junction matrix permits signal assignments to be controlled by the program through interaction with the aid of display device 1, 2.

When switch S2 is in position S2-d, the technician systems 7 to 9 are switched off. The accessed storage areas can be individual storage areas or storage sectors of one or more common storage areas. Switches S1 and S2 represented in the embodiment example as rotary switches, could be replaced by a single control switch. Other combinations of keys located on the control console could also be set in the positions described.

We claim:
1. An x-ray system including an X-ray generator and an x-ray apparatus connected thereto for X-ray diagnosis and/or x-ray treatment, comprising
a program control for controlling the x-ray generator and the x-ray apparatus, the program control having a storage means for storage of a plurality of control values for adjustment of the x-ray generator and the x-ray apparatus, said storage means comprising an anatomic-organ-related program register means for storage of a plurality of organ-related sets of predetermined ones of said control values,
a control console with a plurality of function keys for selection of functions of the program control and with switching means for selection of operation modes of the program control and with alphanumerical display means for display of said control values and with input keys for modifying said control values when displayed on said alphanumerical display means, said plurality of function keys including a group of several function keys for selection of each of said organ-related sets and for displaying said sets on said alphanumerical display means each upon actuation of a corresponding one of said group of several function keys,
said alphanumerical display means comprising two separate alphanumerical display lines, each of a plurality of display digits for displaying said control values by a first one of said display lines and for displaying written text messages of several textual words by a second one of said display lines,
said input keys being assigned to said first one of said display lines for modifying said control values displayed by said first one of said display lines,
said anatomic-organ-related program register means being designed for storing for each of said plurality of organ-related sets a written organ-related textual message to be displayed by said second one of said display lines simultaneously with the displaying of the corresponding one of said organ-related sets of predetermined ones of said control values by said first one of said display lines upon actuation of said corresponding one of said group of several function keys, means at said control console for separately reading each of said organ-related sets of control values and of written text messages into said first and second display lines, respectively, said means for reading comprising an auxiliary storage area of said storage means for organ-related written text messages and their related sets of control values and a means for transferring said messages respectively related sets of control values from said auxiliary storage area to said second one and first one of said display lines respectively upon actuation of a first selector switch of said switching means on the control console, said switching means including a second selector switch for storing a display content of said first and second display lines into said anatomic-organ-related program register means upon actuation of each of said group of several function keys.

2. The x-ray system of claim 1, including means with a keyboard for reading said messages and related sets of control values into said auxiliary storage area.

3. The x-ray system of claim 1, further comprising an electronic monitoring system for monitoring faults, namely operator errors, hardware errors, inappropriate reference values and exceeded limit values for the x-ray generator and the x-ray apparatus, said monitoring system including a second program register of said storage means for storage of written textual fault messages identifying said faults and for individual display of said written fault text messages by said second one of said display lines.

4. The x-ray system according to claim 3, wherein the monitoring system is connected to a fault text message listing storage register of said storage means connectable through a switch arrangement and a third selector switch to said second one of said display lines.

5. The x-ray system of claim 1, wherein said second one of said display lines is connectable through a fourth selector switch of said switching means to a written text storage area of an electronic information system in order to display information that can be called from said written text storage area to said second one of said display lines by means of a selector switch arrangement.

6. The x-ray system of claim 1, wherein the said two separate alphanumerical display lines and a keyboard are connectable to a print buffer whose contents, by means of a fifth selector switch, can be read out into a printer.

7. The x-ray system of claim 1, wherein an integrated programmed electronic test system with a written message text storage area of said storage means is connectable through a switch arrangement and a sixth selector switch of said switching means to said second one of said display lines.

* * * * *